(12) United States Patent
Aylsworth et al.

(10) Patent No.: US 8,875,707 B2
(45) Date of Patent: *Nov. 4, 2014

(54) TRANS-FILL METHOD AND SYSTEM

(75) Inventors: Alonzo C. Aylsworth, Wildwood, MO (US); Kevin G. McCulloh, Simi Valley, CA (US)

(73) Assignee: Respironics, Inc., Murrysville, PA (US)

( * ) Notice: Subject to any disclaimer, the term of this patent is extended or adjusted under 35 U.S.C. 154(b) by 723 days.

This patent is subject to a terminal disclaimer.

(21) Appl. No.: 13/017,652

(22) Filed: Jan. 31, 2011

(65) Prior Publication Data

US 2011/0120461 A1    May 26, 2011

Related U.S. Application Data

(63) Continuation of application No. 11/037,523, filed on Jan. 18, 2005, now Pat. No. 7,900,627.

(51) Int. Cl.
| | |
|---|---|
| *A62B 7/10* | (2006.01) |
| *A62B 19/00* | (2006.01) |
| *A62B 23/02* | (2006.01) |
| *A61M 16/10* | (2006.01) |

(52) U.S. Cl.
CPC .................................... *A61M 16/10* (2013.01)
USPC ............ 128/205.12; 128/205.11; 128/205.27; 128/204.22

(58) Field of Classification Search
USPC ............. 128/202.26, 203.25, 204.18, 204.21, 128/204.22, 205.11, 205.12, 205.27
See application file for complete search history.

(56) References Cited

U.S. PATENT DOCUMENTS

| | | | |
|---|---|---|---|
| 2,160,326 A | | 5/1939 | Carbonara |
| 2,236,084 A | * | 3/1941 | Brown ........................... 138/43 |
| 3,961,869 A | | 6/1976 | Droege |
| 4,406,596 A | | 9/1983 | Budde |
| 4,428,372 A | | 1/1984 | Betsel |
| 4,449,990 A | | 5/1984 | Tedford |
| 4,561,287 A | | 12/1985 | Rowland |
| 4,587,967 A | | 5/1986 | Chu |
| 4,612,928 A | | 9/1986 | Tiep |
| 4,627,860 A | | 12/1986 | Rowland |
| 4,673,415 A | | 6/1987 | Stanford |
| 4,765,804 A | | 8/1988 | Lloyd-Williams |
| 4,838,261 A | | 6/1989 | Von Dem Hagen |
| 4,860,803 A | | 8/1989 | Wells |
| 4,869,733 A | | 9/1989 | Stanford |
| 5,060,514 A | | 10/1991 | Aylsworth |
| 5,071,453 A | | 12/1991 | Hradek |
| 5,078,757 A | | 1/1992 | Rottner |
| 5,144,945 A | | 9/1992 | Nishino |
| 5,195,874 A | | 3/1993 | Odagiri |
| 5,199,423 A | | 4/1993 | Harral |
| 5,237,987 A | | 8/1993 | Anderson |
| 5,248,320 A | | 9/1993 | Garrett |
| 5,313,820 A | | 5/1994 | Aylsworth |
| 5,354,361 A | | 10/1994 | Coffield |

(Continued)

*Primary Examiner* — Valerie L Skorupa
(74) *Attorney, Agent, or Firm* — Michael W. Haas

(57) ABSTRACT

A trans-fill method and system comprising obtaining therapeutic gas from a therapeutic gas source, compressing the therapeutic gas from the therapeutic gas source in at least two stages to create an intermediate therapeutic gas stream and a high pressure therapeutic gas stream, supplying therapeutic gas to a patient from the intermediate therapeutic gas stream, and filling a cylinder with the therapeutic gas from the high pressure therapeutic gas stream substantially simultaneously with supplying therapeutic gas to the patient.

18 Claims, 2 Drawing Sheets

(56) References Cited

U.S. PATENT DOCUMENTS

| | | | |
|---|---|---|---|
| 5,369,979 A | 12/1994 | Aylsworth | |
| 5,405,249 A | 4/1995 | Benson | |
| 5,452,621 A | 9/1995 | Alysworth | |
| 5,474,595 A | 12/1995 | McCombs | |
| 5,584,669 A | 12/1996 | Becker | |
| 5,593,291 A | 1/1997 | Lynn | |
| 5,603,315 A | 2/1997 | Sasso | |
| 5,709,203 A | 1/1998 | Gier | |
| 5,746,806 A | 5/1998 | Aylsworth | |
| 5,858,062 A | 1/1999 | McCulloh | |
| 5,915,834 A | 6/1999 | McCulloh | |
| 5,918,596 A | 7/1999 | Heinonen | |
| 5,979,440 A | 11/1999 | Honkonen | |
| 5,988,165 A | 11/1999 | Richey | |
| 6,131,572 A | 10/2000 | Heinonen | |
| 6,283,119 B1 * | 9/2001 | Bourdon | 128/204.23 |
| 6,302,107 B1 | 10/2001 | Richey, II | |
| 6,314,957 B1 * | 11/2001 | Boissin et al. | 128/204.17 |
| 6,334,468 B1 | 1/2002 | Friestad | |
| 6,342,090 B1 | 1/2002 | Cao | |
| 6,346,139 B1 | 2/2002 | Czabala | |
| 6,393,802 B1 | 5/2002 | Bowser | |
| 6,394,088 B1 | 5/2002 | Frye | |
| 6,402,697 B1 * | 6/2002 | Calkins et al. | 600/532 |
| 6,446,630 B1 | 9/2002 | Todd | |
| 6,478,857 B2 | 11/2002 | Czabala | |
| 6,629,525 B2 * | 10/2003 | Hill et al. | 128/202.26 |
| 6,651,653 B1 | 11/2003 | Honkonen | |
| 6,651,658 B1 | 11/2003 | Hill | |
| 6,681,764 B1 | 1/2004 | Honkonen | |
| 6,698,423 B1 | 3/2004 | Honkonen | |
| 6,701,923 B2 | 3/2004 | Cazenave et al. | |
| 7,066,985 B2 * | 6/2006 | Deane et al. | 95/96 |
| 7,204,249 B1 * | 4/2007 | Richey et al. | 128/204.18 |
| 7,900,627 B2 * | 3/2011 | Aylsworth et al. | 128/205.12 |
| 2003/0005928 A1 * | 1/2003 | Appel et al. | 128/202.26 |
| 2004/0079359 A1 | 4/2004 | Aylsworth | |

* cited by examiner

TRANS-FILL METHOD AND SYSTEM

CROSS-REFERENCE TO RELATED APPLICATIONS

This application is a Continuation under 35 U.S.C. §121 of U.S. patent application Ser. No. 11/037,523, filed 18 Jan. 2005, the contents of which is incorporated herein by reference.

STATEMENT REGARDING FEDERALLY SPONSORED RESEARCH OR DEVELOPMENT

Not applicable.

BACKGROUND OF THE INVENTION

1. Field of the Invention

Embodiments of the present invention are directed to delivery of therapeutic gas to a patient and substantially simultaneously filling portable cylinders.

2. Background of the Invention

Many patients with lung and/or cardiovascular problems are required to breathe therapeutic gas in order to obtain sufficient dissolved oxygen in their blood stream. In home environments, patients may have a pressure-swing absorption (PSA) system comprising a compressor that forces atmospheric air through one or more molecular sieves. The sieve material traps nitrogen, and thus the gas exiting a molecular sieve has an increased oxygen content-oxygen-enriched gas. For this reason, PSA systems may be referred to as oxygen concentration systems and/or oxygen concentrators. While, the oxygen-enriched gas exiting a molecular sieve bed has a pressure of approximately 20 pounds per square inch (PSI), most oxygen concentrators regulate the pressure and continuously deliver therapeutic gas to the patient at approximately 5 PSI. Oxygen-enriched gas at the pressure that the gas exits the molecular sieve bed is not made available to the patient. Stated otherwise, most oxygen concentrators do not have a port from which oxygen-enriched gas at approximately 20 PSI may be supplied.

PSA systems, however, are not generally portable. So that patients may be ambulatory, therapeutic gas may be delivered from a portable cylinder. A portable cylinder, however, provides only limited volume, and therefore periodically needs to be refilled. While it is possible to have these cylinders exchanged or refilled by way of commercial home health care services, some patients have systems within their homes which perform a dual function: filling portable cylinders with oxygen-enriched gas; and providing oxygen-enriched gas to the patient for breathing. Systems such as these have come to be known as "trans-fill" systems.

Trans-fill systems need to produce oxygen-enriched gas having pressure of approximately 2700 PSI to fill a portable cylinder to a full state of approximately 2200 PSI. In order to achieve the pressure sufficient to fill a cylinder, a compressor (also known in the art as an intensifier) is used. However, 5 PSI oxygen-enriched gas may be too low an inlet pressure for an intensifier to create sufficient pressure to fill a portable cylinder. For this reason, related art trans-fill systems are integral systems, combining an oxygen concentrator with an intensifier. The intensifier is supplied oxygen-enriched gas at the pressure the gas exits the molecular sieve bed, approximately 20 PSI, and the patient is provided pressure regulated oxygen-enriched gas at approximately 5 PSI. For example, U.S. Pat. No. 5,858,062 to McCulloh et al. (assigned to Litton Systems, Inc. and thus hereinafter the "Litton patent") discloses an integral system where oxygen-enriched gas exiting a molecular sieve bed of an oxygen concentrator is applied to a plenum. From the plenum, the oxygen-enriched gas is supplied to an intensifier, and also from the plenum the pressure of the oxygen-enriched gas is regulated and supplied to a patient port. Likewise, U.S. Pat. No. 5,988,165 to Richey, II et al. discloses an integral system where, much like the Litton patent, oxygen-enriched gas exiting a molecular sieve bed of an oxygen concentrator is provided to a compressor, and regulated to 5 PSI before being provided to the patient.

Thus, what is needed is a trans-fill method and system that is not constrained to having an integral oxygen concentrator, and thus could use oxygen-enriched gas provided from any third party oxygen concentration system or other source of oxygen-enriched gas.

SUMMARY OF SOME OF THE PREFERRED EMBODIMENTS

The problems noted above are solved in large part by a trans-fill method and system. Some exemplary embodiments may be a method comprising obtaining therapeutic gas from a therapeutic gas source, compressing the therapeutic gas from the therapeutic gas source in at least two stages to create an intermediate therapeutic gas stream and a high pressure therapeutic gas stream, supplying therapeutic gas to a patient from the intermediate therapeutic gas stream, and filling a cylinder with the therapeutic gas from the high pressure therapeutic gas stream substantially simultaneously with supplying therapeutic gas to the patient.

Other illustrative embodiments are a trans-fill device comprising a therapeutic gas inlet port that is supplied therapeutic gas from a therapeutic gas source (at pressures of approximately 3.5 pounds per square inch (PSI) to approximately 6 PSI), a patient port that supplies therapeutic gas to a patient (wherein the patient port supplies the therapeutic gas at a pressure of approximately 20 PSI to approximately 35 PSI, the therapeutic gas taken between a first and second compression stage within the trans-fill device), and a cylinder fill outlet port that supplies therapeutic gas to fill a cylinder to approximately 2200 PSI substantially simultaneously with the patient port supplying therapeutic gas to the patient.

Yet other exemplary embodiments are a trans-fill system comprising a compression system coupled to oxygen-enriched therapeutic gas provided at an inlet of the trans-fill system (the compression system having a first compression stage which creates an intermediate pressure therapeutic gas stream from the oxygen-enriched therapeutic gas at the inlet, and a second compression stage which creates a high pressure therapeutic gas stream from the intermediate pressure therapeutic gas stream), and a conserver coupled to the intermediate pressure therapeutic gas stream (the conserver delivers a bolus of therapeutic gas to a patient during inhalation of the patient). The trans-fill system provides therapeutic gas from the high pressure therapeutic gas stream to a portable cylinder and also substantially simultaneously provides therapeutic gas to the patient.

Yet other illustrative embodiments are a trans-fill system comprising a compression system coupled to a low pressure therapeutic gas stream provided at an inlet of the trans-fill system (the compression system having a first compression stage coupled to the low pressure therapeutic gas stream that creates an intermediate pressure therapeutic gas stream, and a second compression stage coupled to the intermediate pressure therapeutic gas stream that creates a high pressure therapeutic gas stream), a conserver coupled to the intermediate pressure therapeutic gas stream (the conserver delivers a bolus of therapeutic gas to a patient during inhalation of the patient), and an adjustable flow restriction device fluidly coupled to the low pressure therapeutic gas stream. The trans-fill system provides therapeutic gas from the high pressure therapeutic gas stream to a portable cylinder and also substantially simultaneously one of: provides therapeutic gas to the patient through the conserver; or provides therapeutic gas to the patient through the adjustable flow restriction device.

The disclosed devices and methods comprise a combination of features and advantages which enable it to overcome the deficiencies of the prior art devices. The various characteristics described above, as well as other features, will be readily apparent to those skilled in the art upon reading the following detailed description, and by referring to the accompanying drawings.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct connection. Thus, if a first device couples to a second device, that connection may be through a direct connection, or through an indirect connection via other devices and connections.

DETAILED DESCRIPTION OF THE PREFERRED EMBODIMENTS

Trans-fill systems in accordance with embodiments of the invention comprise both electrical components and mechanical components. In order to differentiate between electrical connections and fluid connections, FIGS. 1 and 2 illustrate electrical connections between devices with dash-dot-dash lines, and fluid connections, e.g. tubing connections between devices, with solid lines.

Figure 1:
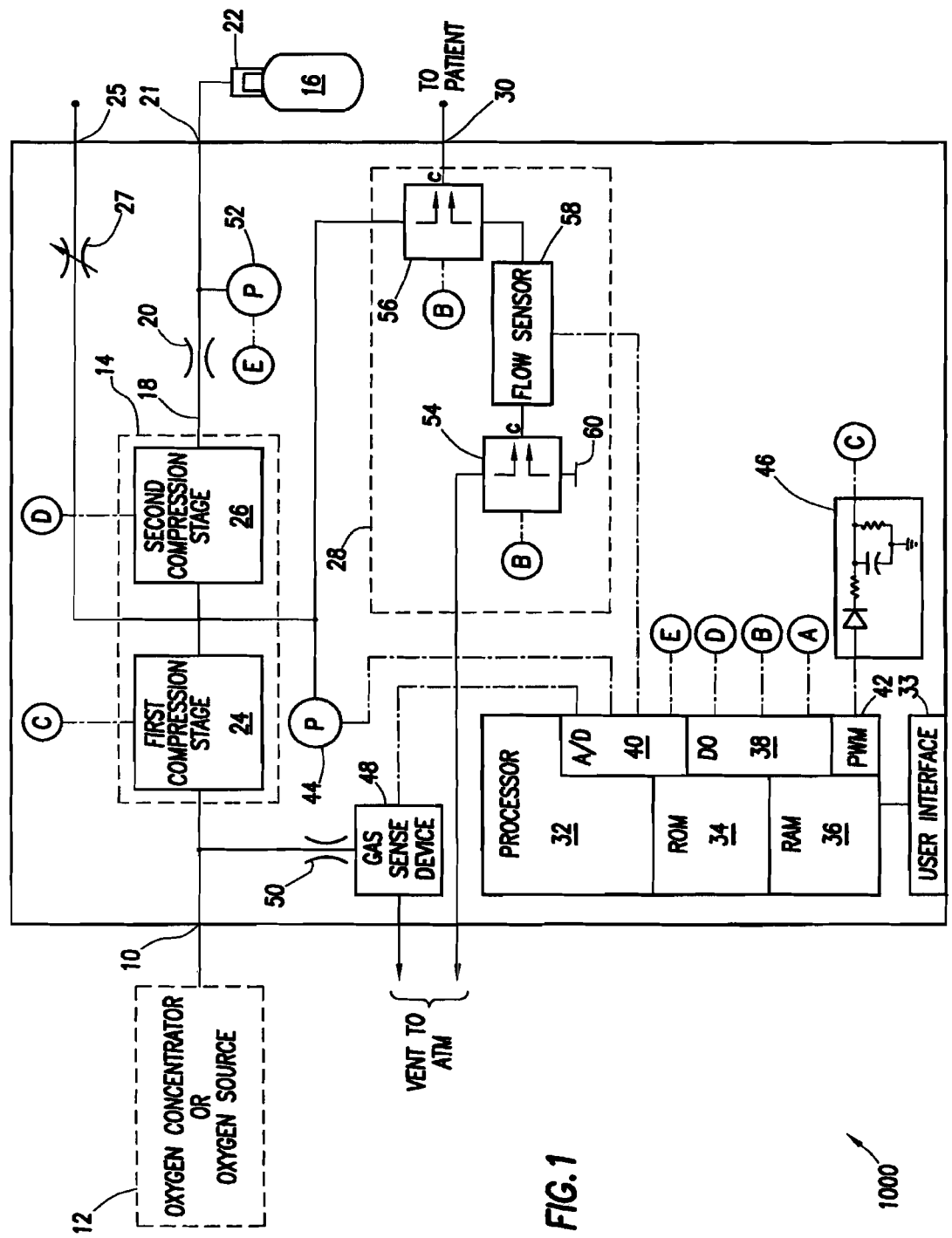
FIG. 1 illustrates a system for providing therapeutic gas to the patient and for filling portable cylinders in accordance with at least some embodiments of the invention.
Figure 2:
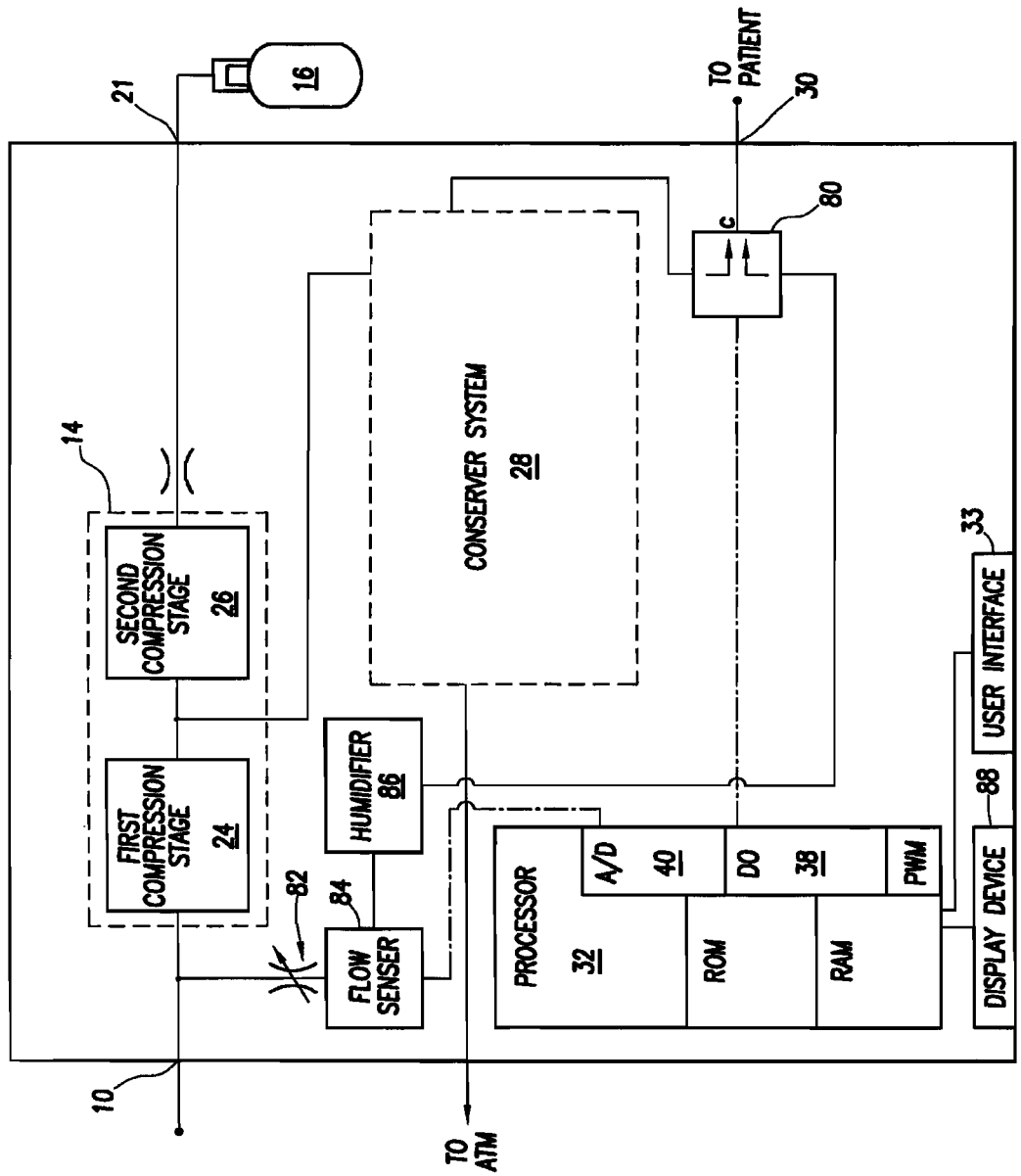
FIG. 2 illustrates a trans-fill system in accordance with alternative embodiments.

FIG. 1 illustrates a trans-fill system in accordance with embodiments of the invention. The trans-fill system 1000 comprises a therapeutic gas inlet port 10 that couples to a source of therapeutic gas. In accordance with at least some embodiments, the therapeutic gas inlet port couples to an oxygen source or oxygen concentrator 12. The oxygen concentrator 12 may be any suitable device for increasing the oxygen content of therapeutic gas delivered to a patient. For example, the oxygen concentrator 12 may be a pressure-swing absorption (PSA) system having a plurality of molecular sieve beds operated in a parallel relationship. In a PSA system, atmospheric air drawn through an air inlet is compressed by a compressor internal to the oxygen concentrator 12 and applied to a molecular sieve bed. In the sieve bed, nitrogen molecules are trapped, and oxygen and argon molecules flow through substantially unimpeded. By removing the nitrogen from the atmospheric air, the concentration of oxygen in the gas exiting the sieve bed may be relatively high, e.g. 90% oxygen or more. While coupling to a PSA system is preferred, a trans-fill system in accordance with embodiments of the invention may couple to any device or system capable of making and/or delivering therapeutic gas.

In accordance with embodiments of the invention, the therapeutic gas inlet port 10 accepts therapeutic gas from a low pressure therapeutic gas stream having pressures of approximately 3.5 pounds per square inch (PSI) to approximately 6 PSI, and preferably 5 PSI. Because trans-fill system 1000 is capable of operating with therapeutic gas inlet pressures in the 3.5 PSI to 6 PSI range, trans-fill system 1000 may couple to the patient port of substantially any commercially available oxygen concentrator, and thus the trans-fill system 1000 need not have an integral oxygen concentrator 12.

In order to increase the pressure of the low pressure therapeutic gas stream, trans-fill system 1000 comprises a compression system 14 which takes the low pressure therapeutic gas and increases the pressure to a pressure sufficient to fill a cylinder, e.g., portable cylinder 16. In accordance with at least some embodiments, the compression system 14 increases the pressure of the low pressure therapeutic gas stream to create a high pressure therapeutic gas stream of approximately 2700 PSI, e.g., at point 18. The high pressure therapeutic gas stream flows through a flow restrictor 20 and then to the portable cylinder 16 by way of a cylinder fill outlet port 21 and a cylinder fill connector 22. The flow restrictor 20 may take any suitable form, e.g., an orifice plate or possibly a section of tubing having relatively small internal diameter (ID).

A compression system 14 in accordance with embodiments of the invention comprises at least two stages. A first compression stage 24 increases the pressure of the low pressure therapeutic gas stream to create an intermediate pressure gas stream of approximately 20 PSI to 35 PSI, with 20 PSI being preferred. The second compression stage 26 increases pressure of the intermediate pressure therapeutic gas stream to create the high pressure therapeutic gas stream. In accordance with a least some embodiments of the invention, the first compression stage 24 is a diaphragm pump (discussed more fully below), and therefore indeed represents a single stage; however, though the illustrated embodiments of FIG. 1 show only a first compression stage 24 and a second compression stage 26, these stages themselves may comprise multiple compression stages, and thus FIG. 1 should not be construed to limited the actual number of compression stages contained within either of the illustrative first compression stage 24 or second compression stage 26.

A trans-fill system in accordance with embodiments of the invention has the ability to fill a portable cylinder 16, and also substantially simultaneously provide therapeutic gas to a patient. In accordance with at least some embodiments, therapeutic gas is provided to the patient from the intermediate pressure therapeutic gas stream created by the first compression stage 24. In particular, the intermediate pressure therapeutic gas stream fluidly couples to a conserver system 28. The conserver system 28 fluidly couples to a patient by way of a patient port 30, e.g., a DISS port coupled to a nasal cannula. The conserver system 28 senses an inhalation of a patient and provides a bolus of therapeutic gas on substantially each inhalation—conserve mode operation. Supplying a conserver system with oxygen-enriched gas in the illustrative 20 PSI to 33 PSI range advantageously increases the efficiency of the conserving system 28, and also advantageously increases the possible distance between the trans-fill device and the patient. For example, having an intermediate pressure therapeutic gas stream in the illustrative 20 PSI to 35 PSI range allows for conserve mode operation with tubing lengths between the trans-fill device and nasal cannula of the patient of 50 feet or more. U.S. Pat. Ser. No. 10/287,899, titled, "Therapeutic Gas Conserver and Control," incorporated by reference herein as if reproduced in full below, discloses a conserver system with extended range capabilities.

Trans-fill systems in accordance with embodiments of the invention also comprise a processor 32. The processor 32 may be a microcontroller, and therefore the microcontroller may be integral with read only memory (ROM) 34, random access memory (RAM) 36, a digital output (DO) module 38, an analog-to-digital converter (A/D) 40 and a pulse width modulation (PWM) module 42. Although a microcontroller may be preferred because of the integrated components, in alternative embodiments the processor 32 may be implemented as a standalone central processing unit in combination with individual ROM, RAM, DO, A/D and PWM devices.

The ROM 34 stores instructions executable by the processor 32. In particular, the ROM 34 comprises software programs that implement control of the compression system 14, as well as control of the conserver system 28. The RAM 36 is the working memory for the processor 32, where data is temporarily stored and from which instructions are executed. Processor 32 couples to other devices within the trans-fill system by way of the analog-to-digital converter 40, the digital output module 38, and the pulse-width module 42.

Pressure sensor 44 fluidly couples to the intermediate pressure therapeutic gas stream, and electrically couples to the analog-to-digital converter 40. Pressure sensor 44 may be a part no. MPX4250DP pressure transducer available from Motorola, Inc. of Schaumburg, Ill. Software executed by processor 32 reads the pressure of the intermediate pressure therapeutic gas stream using pressure sensor 44. If the pressure is greater than a set point pressure, then the processor 32 changes a speed command coupled to the first compression stage 24, possibly by way of pulse-width modulation module 42. In accordance with embodiments of the invention, the first compression stage 24 is a diaphragm pump having part number D827-23-01 produced by Hargraves Technology Corporation of Mooresville, N.C. The illustrative Hargraves diaphragm pump is a combined diaphragm pump, motor and motor control system that controls speed of oscillation of the diaphragm (and therefore outlet pressure/flow) based on a 0 volt to 5 volt control input.

Thus, in accordance with these embodiments of the invention, processor 32, executing a program, reads the pressure of the intermediate pressure therapeutic gas stream, and produces a pulse-width modulated output through the module 42 that electrically couples to the control input of the first compression stage 24. In order to convert the pulse-width modulated output to a 0 volt to 5 volt control signal, the trans-fill system 1000 has an averaging circuit 46. Averaging circuit 46 comprises a diode in combination with a RC filter, which takes the pulse width modulated signal created by the module 42 and creates a 0 volt to 5 volt control signal applied to the diaphragm pump. In alternative embodiments of the invention, the processor 32 directly creates the 0 volt to 5 volt control signal by use of a digital-to-analog (D/A) converter (not specifically shown). In yet further alternative embodiments, a different first compression stage device or devices may be used, and these devices may utilize different types of control inputs. Inasmuch as the pressure of the intermediate pressure therapeutic gas stream is controlled by the first compression stage 24, the pressure of the therapeutic gas stream may be outside the preferred 3.5 PSI to 6 PSI range without departing from the scope and spirit of the invention.

The compression system 14 in accordance with embodiments of the invention also comprises a second compression stage 26. As discussed above, the second compression stage takes the intermediate pressure therapeutic gas stream and produces the high pressure therapeutic gas stream. The second compression stage 26 is also controlled by the processor 32. In accordance with some embodiments of the invention, the second compression stage 26 is a compressor or intensifier, such as a part number 2003336-1 intensifier (itself having multiple stages) produced through Chad Therapeutics, Inc. of Chatsworth, Calif. In alternative embodiments, the second compression stage is a wobble-piston compressor, such as described in U.S. Pat. No. 6,302,107, or a linear cylinder used as a compressor. Inasmuch as the pressure of the intermediate pressure therapeutic gas stream is controlled, the second compression stage 26 need not necessarily have the ability to produce a variable outlet pressure, and may be controlled as an on-off device. In these embodiments then, processor 32, executing a program, selectively turns on and off the second compression stage 26 by selectively asserting and deasserting a digital output from digital output module 38.

In accordance with at least some embodiments, the times at which the illustrative second compression stage is operational is a function of both the oxygen concentration of the low pressure therapeutic gas stream, and the status of the fill of the portable cylinder 16. With regard to oxygen concentration, a gas sense device 48 fluidly couples to the therapeutic gas inlet port 10 by way of a flow restriction device 50. In some embodiments, the gas sense device 48 is an oxygen-selective sensor, such as sensors based on zirconium oxide, galvanic, or paramagnetic technologies. If the gas sense device 48 is an oxygen-selective sensor, the device analyzes the actual percentage of oxygen in the gas. Alternatively, the gas sense device 48 is a time-of-flight density sensor that measures density, and thus purity, of a gas stream. By taking a relatively small sample of the therapeutic gas provided at the therapeutic gas inlet port, e.g. 5 cubic centimeters (cc) per minute, the gas sense device 48 determines the oxygen concentration or purity of the therapeutic gas. Processor 32, executing a program, reads the oxygen concentration or purity of the therapeutic gas determined by gas sense device 48, possibly through analog-to-digital converter 40, and only commands the second compression stage 26 to be operational when the oxygen concentration is approximately 90% or above. If the oxygen concentration falls below approximately 90%, processor 32, executing a program, turns off the second compression stage 26, and thus ceases filling the cylinder. In the event oxygen concentration increases again to approximately 90% or above, the second compression stage 26 (and first compression stage 24 if it too was turned off (see discussion of FIG. 2 below)) restarts and resumes filling of the portable cylinder.

The second situation when the second compression stage 26 is turned off is when filling of the portable cylinder 16 is complete. To this end, pressure sensor 52 fluidly couples to the therapeutic gas within the portable cylinder 16 downstream of the flow restrictor 20, and electrically couples to analog-to-digital converter 40. In accordance with some embodiments pressure sensor 52 is a part no. MLH03KPSP01A pressure transducer available from Honeywell of Morris Township, N.J. Thus processor 32, executing a program, senses pressure of the therapeutic gas within the portable cylinder 16. When the pressure reaches a predetermined threshold, e.g. 2200 PSI, the fill of the portable cylinder 16 is complete, and in this situation the second compression stage 26 is turned off by the processor 32 selectively asserting or deasserting the associated digital output.

In spite of the fact that the second compression stage 26 may have been turned off, either because the oxygen concentration falls below approximately 90%, or the portable cylinder 16 is full, the first compression stage 24 may remain operational, providing intermediate pressure therapeutic gas to the conserver system 28. If oxygen concentration falls below 85%, the patient is still provided therapeutic gas, but the patient is notified of the low oxygen concentration by way of an alarm, and size of the bolus may increase to ensure proper blood oxygen saturation of the patient. Continuing to supply therapeutic gas in bolus form reduces the draw on the upstream oxygen concentrator, and may thus give the oxygen concentrator an opportunity to recover. If the oxygen concentration continues to drop, therapeutic gas delivery may transition to a continuous delivery mode, either through one or more valves of the conserver system 28 and reduced outlet pressure of the first compression stage 24, or the trans-fill system 1000 may shut off the first compression stage 24 and supply the patient in a continuous mode directly from the low pressure therapeutic gas stream (discussed more fully below with respect to FIG. 2).

Although the conserver system 28 may be any currently available or after-developed electronic or pneumatic conserver, in accordance with at least some embodiments of the invention the conserver system 28 is implemented utilizing three-port valve 54, three-port valve 56 and a flow sensor 58. Each three-port valve may be a 5-volt solenoid operated valve that selectively fluidly couples one of two ports to a common port (labeled as C in the drawings). Three-port valves 54 and 56 may be Humphrey Mini-Mizers having part number D3061A available from the John Henry Foster Company of St Louis, Mo. By selectively applying voltage on a digital output signal line coupled to the three-port valve 56, the processor 32 is able to: couple the intermediate pressure therapeutic gas stream to the common port and therefore to the patient port 30 and patient; or couple the flow sensor 58 to the common port and therefore to the patient port 30 and patient. Thus, during the period of time when the trans-fill system 1000 provides therapeutic gas to the patient, three-port valve 56 couples the intermediate pressure therapeutic gas stream to the patient port 30 and also blocks the flow through flow sensor 58. The length of time that the three-port valve 56 couples the intermediate pressure therapeutic gas stream to the patient is a function of the bolus size setting, which may be communicated to the trans-fill system by way of a user interface 33 coupled to the processor. In some embodiments, the user interface 33 is a dial-type input (not specifically shown) where a patient dials in a bolus size setting. In alternative embodiments, user interface 33 is a key pad or keyboard, and corresponding display device, where bolus size is supplied to the processor 32 in digital format.

In the second valve position of three-port valve 56, flow sensor 58 is fluidly coupled to the patient port 30, and therefore the patient, to allow sensing of a patient's inhalation. In accordance with some embodiments of the invention, flow sensor 58 is a flow-through mass flow sensor having part no. AWM92100V available from Microswitch (a division of Honeywell). Thus, the flow sensor 58 will not function until gas can flow through the sensor. Three-port valve 54, in a first valve position, fluidly couples flow sensor 58 to an atmospheric vent, and thus allows gas to flow through the flow sensor for measurement purposes. The three-port valve 54, in a second valve position, couples a blocked port 60 to the common port (the purpose of which is discussed below).

Consider for the purposes of explanation a trans-fill systems 1000 having at least the first compression stage operational. In the first configuration of the three-port valves 54 and 56, the flow sensor 58 fluidly couples to the patient port 30, and therefore the patient. As the patient begins to inhale, processor 32, executing a program, reads or senses the inhalation through flow sensor 58. When the inhalation is sensed, processor 32 commands three-port valve 56 to change positions. Three-port valve 56 thus couples the intermediate pressure therapeutic gas stream to the common port, and therefore to the patient port 30 and patient. In this configuration, a bolus of therapeutic gas is delivered to the patient. For a period of time, determined by the patient's bolus size setting, the bolus is delivered, and thereafter the processor 32 commands the three-port valve 56 to again couple the flow sensor 58 to the common port. However, just as valve 56 couples the patient to the flow sensor 58 to the common port, three-port valve 54 couples the blocked port 60 to its common port, thus blocking reverse flow of therapeutic gas through the flow sensor 58. After sufficient time has passed to allow the therapeutic gas to propagate to the patient and/or to allow the pressure in the tubing between the trans-fill system and patient to dissipate, the processor 32 commands the three-port valve 54 to couple the atmospheric vent to its common port, thus allowing flow through the flow sensor 58, and enabling the processor 32 and flow sensor 58 to sense the next inhalation.

Although the illustrative embodiment of FIG. 1 shows only one conserve mode flow path, in alternative embodiments a plurality of conserve mode flow paths may be present. For example, the trans-fill system 1000 may individually sense and selectively deliver therapeutic gas to one or more of the patient's left naris, right naris and/or mouth. U.S. patent application Ser. No. 10/697,232, titled, "Method and System of Sensing Airflow and Delivering Therapeutic Gas to a Patient," incorporated by reference herein as if reproduced in full below, discloses a system for individually sensing, and selectively delivering, therapeutic gas to a patient.

The trans-fill system of FIG. 1 also comprises a nebulizer port 25 coupled to the intermediate pressure therapeutic gas stream, through adjustable flow control device 27. Nebulizer port 25 allows a patient to administer nebulizer treatments, and nebulizer devices may need therapeutic gas pressures in the 20-35 PSI range. In alternative embodiments, a patient may perform nebulizer treatments by fluidly coupling the nebulizer device to the patient port 30 with the valve 56 set to, over the course of the treatment, couple the intermediate pressure gas stream to the port 30. In these alternative embodiments, flow control device 27 would fluidly couple between the first compression stage 24 and the valve 56 or between the valve 56 and the patient port 30.

FIG. 2 illustrates a trans-fill system 2000 in accordance with alternative embodiments of the invention. The trans-fill system 2000, in addition to the capabilities discussed with respect to FIG. 1, has the ability to provide therapeutic gas to a patient in a continuous flow mode from the low pressure therapeutic gas stream. In particular, the trans-fill system comprises a therapeutic gas inlet port 10 that fluidly couples to compression system 14. Much like the embodiments discussed with respect to FIG. 1, the compression system 14 comprises a first compression stage 24 that creates an intermediate pressure therapeutic gas stream. The intermediate pressure therapeutic gas stream fluidly couples to both conserver system 28 and the second compression stage 26. The compression system 14 also comprises a second compression stage 26 that creates a high pressure therapeutic gas stream. The high pressure therapeutic gas stream fluidly couples to and fills portable cylinder 16 by way of cylinder fill outlet port 21. In some modes of operation, the trans-fill device 2000 simultaneously fills portable cylinder 16, and supplies therapeutic gas to a patient using the conserver system 28 through three-port valve 80. Other than the conserver system 28 coupling to the patient port 30 through the three-port valve 80, operation of the trans-fill system 2000 in this mode is as described with respect to FIG. 1. Several of the components of FIG. 1, e.g., ges sense device, pressure sensors and nebulizer port, are not included in FIG. 2 so as not to unduly complicate the figure, but are inherently present.

In other modes of operation, the trans-fill system 2000 provides therapeutic gas to a patient in a continuous flow mode from the low pressure therapeutic gas stream. In particular, trans-fill system 2000 comprises an adjustable flow control device 82 coupled to the therapeutic gas inlet port 10. In some embodiments, the adjustable flow control device 82 allows a patient to set or adjust the mass flow of therapeutic gas. In alternative embodiments, the adjustable flow control device 82 is controlled by the processor 32, e.g., processor 32 controlling a servomotor mechanically coupled to a needle valve. The therapeutic gas stream whose flow rate is set by the adjustable flow restrictor 82 fluidly couples to a flow sensor 84. Flow sensor 84 could be a part number AWM43600V available from Microswitch (a division of Honeywell). Thus, in modes where the trans-fill system 2000 is delivering therapeutic gas in a continuous flow mode, flow sensor 84 (electrically coupled to processor 32 by way of the analog-to-digital converter 40) reads the mass flow and provides the information to a program executing on the processor 32.

Patients provided therapeutic gas in a continuous flow mode have a tendency to experience discomfort attributable, to some extent, to nasal drying effects. Thus, in continuous flow mode it is beneficial to humidify the therapeutic gas. In accordance with some embodiments, trans-fill system 2000 comprises a humidifier bottle 86 fluidly coupled to the low pressure therapeutic gas stream provided to the patient. After humidification, therapeutic gas couples to the patient port 30 by way of the three-port valve 80.

Still referring to FIG. 2, consider the trans-fill system 2000 supplying therapeutic gas to a patient in a continuous flow mode. In this continuous flow mode, the patient and/or processor 32 may adjust the flow rate of therapeutic gas using the adjustable flow control device 82. Flow sensor 84 senses the instantaneous mass flow, and that mass flow may be read by processor 32. So that the patient too may see the instantaneous therapeutic gas flow rate, the trans-fill system 2000 comprises a display device 88 coupled to the processor 32. The display device 88 could be, for example, a liquid crystal display capable of showing both text and graphics. In these embodiments, display device 88 couples to the processor 32 by way of a digital communications port (not specifically shown). In alternative embodiments, the display device could be a series of light emitting diodes that illuminate to indicate a particular flow rate. In these embodiments, the display device 88 couples to the processor 32 by a digital-to-analog output (not specifically shown) or the digital output module 38. Regardless of the precise form of the display device 88, display device 88 communicates to the patient the instantaneous flow rate of therapeutic gas provided in a continuous flow mode.

Depending on the capabilities of the oxygen concentrator or oxygen source supplying the low pressure therapeutic gas stream, trans-fill system 2000 may be capable of simultaneously filling portable cylinder 16 and providing therapeutic gas to a patient in continuous flow mode. Consider, for example, an upstream oxygen concentrator (not shown in FIG. 2) that has the capability of delivering oxygen-enriched gas at a rate of 5 liters per minute (LPM). If the fill rate of the portable cylinder 16 is an illustrative 2 LPM, then the trans-fill system 2000 may be capable of simultaneously delivering therapeutic gas to the patient in continuous flow mode of up to 3 LPM while simultaneously filling the portable cylinder 16. If the patient's continuous flow prescription or setting exceeds 3 LMP, then trans-fill system 2000 transitions to delivering therapeutic gas to the patient in a conserve mode. In particular, processor 32, executing the program, fluidly couples the conserve system 28 to the patient port 30 by commanding the valve position of three-port valve 80. Thus, in this mode of operation, the trans-fill system 2000 provides a bolus of therapeutic gas to the patient on substantially each inhalation, with the size of the bolus (length of time that gas is delivered) based on a bolus size setting communicated to the processor 32 by way of user interface 33. When filling of the portable cylinder is complete, or where filling has stopped because of low oxygen concentration, continuous delivery of therapeutic gas may resume.

In systems where the first compression stage 24 is a diaphragm pump, flow through diaphragm pump is relatively continuous, and thus a trans-fill system in accordance with the embodiments above need not have a low pressure therapeutic gas stream buffer tank. In alternative embodiments of the invention, the first stage compression device 24 may be a linear cylinder driven by compressed air. In these embodiments, the therapeutic gas flow into the linear cylinder may be very cyclic (high flow as the linear cylinder draws therapeutic gas, and no flow during the compression stage), and thus a buffer tank on the low pressure therapeutic gas stream may be needed.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A trans-fill system comprising:
an initial compressor configured to generate a low pressure gas stream from ambient gas;
an oxygen concentrator configured to receive the low pressure gas stream and produce a low pressure oxygen-enriched gas stream;
a compression system that receives the low pressure oxygen-enriched gas stream at an inlet, the compression system having a first compression stage that creates an intermediate pressure oxygen-enriched gas stream from the low pressure oxygen-enriched gas stream, and a second compression stage that creates a high pressure oxygen-enriched gas stream from the intermediate pressure oxygen-enriched gas stream;
a conserver coupled to the intermediate pressure oxygen-enriched gas stream, the conserver adapted to deliver a bolus of therapeutic gas to a patient during at least a portion of an inhalation cycle of the patient; and
a fill port operatively coupled to the high pressure oxygen-enriched gas stream, wherein filling a storage vessel via the fill port is provided substantially simultaneously with providing therapeutic gas via the conserver.

2. The trans-fill system as defined in claim 1, wherein the low pressure oxygen-enriched gas stream has a pressure of approximately 3.5 pounds per square inch (PSI) to approximately 6 PSI.

3. The trans-fill system as defined in claim 1, wherein the intermediate pressure oxygen-enriched gas stream has a pressure of approximately 20 pounds per square inch (PSI) to 35 PSI.

4. The trans-fill system as defined in claim 1, wherein the high pressure oxygen-enriched gas stream has a pressure of approximately 2700 pounds per square inch (PSI).

5. The trans-fill system as defined in claim 1, wherein the compression system further comprises a diaphragm pump having an inlet coupled to the low pressure oxygen-enriched gas stream, and wherein the diaphragm pump creates the intermediate pressure oxygen-enriched gas stream.

6. The trans-fill system as defined in claim 5, wherein the diaphragm pump creates the intermediate pressure oxygen-enriched gas stream having a pressure of approximately 20 pounds per square inch (PSI) to approximately 35 PSI.

7. The trans-fill system as defined in claim 1, wherein the trans-fill system does not utilize a buffer tank to buffer oxygen-enriched therapeutic gas provided at the inlet.

8. The trans-fill system as defined in claim 1, further comprising: a gas monitoring device coupled to the oxygen-enriched therapeutic gas provided at the inlet, the gas monitoring device operable to detect purity of the therapeutic gas, and wherein the trans-fill system does not provide therapeutic gas to the storage vessel if the oxygen concentration of the oxygen-enriched therapeutic gas falls below 90%.

9. The trans-fill system as defined in claim 8, wherein the gas monitoring device further comprises an oxygen-specific sensor.

10. The trans-fill system as defined in claim 8, wherein the gas monitoring device further comprises a density sensor.

11. A trans-fill system the system comprising:
an initial compressor configured to generate a low pressure gas stream from ambient gas;
an oxygen concentrator configured to receive the low pressure gas stream and produce a low pressure oxygen-enriched therapeutic gas stream;
a compression system that receives the low pressure oxygen-enriched therapeutic gas stream at an inlet, the compression system having a first compression stage coupled to the low pressure oxygen-enriched therapeutic gas stream that creates an intermediate pressure oxygen-enriched therapeutic gas stream from the low pressure oxygen-enriched therapeutic gas stream, and a second compression stage coupled to the intermediate pressure oxygen-enriched therapeutic gas stream that creates a high pressure oxygen-enriched therapeutic gas stream from the intermediate pressure oxygen-enriched therapeutic gas stream;
a conserver coupled to the intermediate pressure oxygen-enriched therapeutic gas stream, the conserver adapted to deliver a bolus of oxygen-enriched therapeutic gas to a patient during at least a portion of an inhalation cycle of the patient;
an adjustable flow restriction device fluidly coupled to the low pressure oxygen-enriched therapeutic gas stream, and wherein the trans-fill system provides oxygen-enriched therapeutic gas from the high pressure oxygen-enriched gas stream to a storage vessel and also substantially simultaneously one of: (a) provides oxygen-enriched therapeutic gas through the conserver, or (b) provides oxygen-enriched therapeutic gas through the adjustable flow restriction device.

12. The trans-fill system as defined in claim 11, wherein the low pressure oxygen-enriched therapeutic gas stream has a pressure of approximately 3.5 pounds per square inch (PSI) to approximately 6 PSI.

13. The trans-fill system as defined in claim 11, wherein the intermediate pressure oxygen-enriched therapeutic gas stream has a pressure of approximately 20 pounds per square inch (PSI) to 35 PSI.

14. The trans-fill system as defined in claim 11, wherein the high pressure oxygen-enriched therapeutic gas stream has a pressure of approximately 2700 pounds per square inch (PSI).

15. The trans-fill system as defined in claim 11, further comprising a humidifier system fluidly coupled to the low pressure oxygen-enriched therapeutic gas stream.

16. A system comprising:
means for generating a low pressure gas stream from ambient gas;
means for receiving the low pressure gas stream and producing a low pressure oxygen-enriched therapeutic gas stream;
means for receiving the low pressure oxygen-enriched therapeutic gas stream;
first means for compressing the low pressure oxygen-enriched therapeutic gas stream to create an intermediate pressure oxygen-enriched therapeutic gas stream from the low pressure oxygen-enriched gas stream;
second means for compressing the intermediate pressure oxygen-enriched therapeutic gas stream to create a high pressure oxygen-enriched therapeutic gas stream from the intermediate pressure oxygen-enriched therapeutic gas stream; and
means for delivering oxygen-enriched therapeutic gas to a patient from the intermediate pressure oxygen-enriched therapeutic gas stream substantially simultaneously with providing the high pressure oxygen-enriched therapeutic gas stream to a storage vessel, wherein the means for delivering includes a means for conserving coupled to the intermediate pressure therapeutic gas stream, the means for conserving configured to deliver a bolus of therapeutic gas to the patient during at least a portion of an inhalation cycle of the patient.

17. The system as defined in claim 16, further comprising: means for executing programs electrically coupled to the first means for compressing, wherein the means for executing programs controls the first means for compressing to control a pressure of the intermediate pressure oxygen-enriched therapeutic gas stream.

18. The system as defined in claim 17, further comprising: means for monitoring an oxygen concentration of oxygen-enriched therapeutic gas, and means for sensing fluidly coupled to the oxygen-enriched therapeutic gas and electrically coupled to the means for executing; wherein the means for executing refrains from filling the cylinder when the means for sensing detects that an oxygen concentration of the oxygen-enriched therapeutic gas falls below approximately 90%.

* * * * *